(12) United States Patent
Reeves et al.

(10) Patent No.: US 9,284,538 B2
(45) Date of Patent: *Mar. 15, 2016

(54) GENES ENCODING KEY CATALYZING MECHANISMS FOR ETHANOL PRODUCTION FROM SYNGAS FERMENTATION

(71) Applicant: Coskata, Inc., Warrenville, IL (US)

(72) Inventors: Andrew Reeves, Chicago, IL (US); Rathin Datta, Chicago, IL (US)

(*) Notice: Subject to any disclaimer, the term of this patent is extended or adjusted under 35 U.S.C. 154(b) by 150 days.

This patent is subject to a terminal disclaimer.

(21) Appl. No.: 14/083,007

(22) Filed: Nov. 18, 2013

(65) Prior Publication Data

US 2014/0206054 A1    Jul. 24, 2014

Related U.S. Application Data

(60) Division of application No. 12/802,560, filed on Jun. 9, 2010, now Pat. No. 8,628,943, which is a continuation-in-part of application No. 12/336,278, filed on Dec. 16, 2008, now Pat. No. 8,039,239.

(51) Int. Cl.
| | |
|---|---|
| C12P 7/06 | (2006.01) |
| C12N 9/12 | (2006.01) |
| C12N 9/10 | (2006.01) |
| C12N 15/52 | (2006.01) |
| C12N 15/74 | (2006.01) |

(52) U.S. Cl.
CPC ............ *C12N 9/1029* (2013.01); *C12N 9/1217* (2013.01); *C12N 15/52* (2013.01); *C12N 15/74* (2013.01); *C12P 7/065* (2013.01); *Y02E 50/17* (2013.01)

(58) Field of Classification Search
None
See application file for complete search history.

(56) References Cited

U.S. PATENT DOCUMENTS 8,039,239 B2 * 10/2011 Reeves ............................. 435/161
8,628,943 B2 *  1/2014 Reeves et al. ................... 435/161

FOREIGN PATENT DOCUMENTS

| WO | 9527064 A1 | 10/1995 |
| WO | 2008018930 A2 | 2/2008 |
| WO | 2008021141 A2 | 2/2008 |
| WO | 2008028055 A1 | 3/2008 |
| WO | 2008122354 A1 | 10/2008 |
| WO | 2009112334 A2 | 9/2009 |
| WO | 2009154788 A1 | 12/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kopke, M., et al., Clostridium ljungdahlii represents a microbial production platform based on syngas, Proc. Natl. Acad. Sci., (2010), 107:13087-13092.
Abrini, et al., *Clostridium autoethanogenunn*, sp nov., an anerobic bacterium that produces ethanol from carbon monoxide; Arch Microbiol (1994), 161:345-351.
Allen, et al., Factors involved in the electroporation-induced transformation of clostridium peljringens; FEMS Microbiology Letters (1990), 70:217-220.
Tyurin, et al., Electrotransformation of Clostridium acetobutylicum AICC 824 using high-voltage radio frequency modulated square pulses; Journal of Applied Microbiology, 88(2):220-227.
Bark, et al., Biological Production of Alcohols from Coal Through Indirect Liquefaction; Applied Biochemistry and Biotechnology; 18(1):363-378.
Burdette, et al., Purification of acetaldehyde dehydrogenase and alcohol dehydrogenases from Thermoanaerobacter ethanolicus 39 E and characterization of the secondary-alcohol dehydrogenase (2 Adh) as a bifunctional alcohol dehydrogenase-acetyl-CoA reductive thioesterase; Biochem, J. (1994) 302:163-170.
Parke, Construction of mobilizable vectors derived from plasmids RP4, pUC18, and pUC19; Gene (1990) 93:135-137.
Ferry, CO Dehydrogenase, Annual Review of Microbiology (1994), 49:305-333.
Green, et al., Genetic manipulation of acid formation pathways by gene inactivation in clostridium acetobutylicum ATCC 824: Microbiology (1996) 142:2079-2086.
Hensgens, et al., Purification and Characterization of a Benzylviologen-linked, Tungsten-Containing Aldehyde Oxidoreductase from Desulfovibrio Gigas; Journal of Bacteriology, (1995) 177:6195-6200.
Lefranciois, et al., Electrotransformation of *Streptococcus pneumoniae*; evidence for restriction of DNA on entry; Microbiology (1997)143:523-526.
Lin, et al, Transformation of Heat-Treated Clostridium Acetobutylicum Protoplasts with pUB110 Plasmid DNA; Applied and Environmental microbiology, (1984) 48:737-742.
Liou, et al., *Clostridium carboxidivorans* sp. nov., a solvent-producing *clostridium* isolated from an agricultural settling lagoon, and reclassification of the acetogen *Clostridium scatologenese* strain SL1 as *Clostridium drakei* sp. nov.; International Journal of Systematic and Evolutionary Microbiology, (2005) 55:2085-2091.
Liu, et al., Construction and Characterization of ack Deleted mutant Clostridium tyrobutyricum for Enhanced Butyric Acid and hydrogen Production; Biotechnol. Prog., (2006) 22:1265-1275.
Lyras, et al, Conjugative transfer of RP4-oriT shuttle Vectors from *Escherichia coil* to *Clostridium perfringens*; Plasmid, (1998) 39:160-164.
Monod, et al., Sequence and properties of pIM13, a Macrolide-Lincosamide-Streptogramin B Resistance Plasmid from Bacillus subtills; Journal of Bacteriology (1986) 167:138-147.

(Continued)

*Primary Examiner* — Christian Fronda
(74) *Attorney, Agent, or Firm* — McDonnell Boehnen Hulbert & Berghoff LLP

(57) ABSTRACT

Gene sequences of key acetogenic clostridial species were sequenced and isolated. Genes of interest were identified, and functionality was established. Key genes of interest for metabolic catalyzing activity in clostridial species include a three-gene operon coding for CODH activity, a two-gene operon coding for PTA-ACK, and a novel acetyl coenzyme A reductase. The promoter regions of the two operons and the acetyl coA reductase are manipulated to increase ethanol production.

2 Claims, 8 Drawing Sheets

(56) References Cited

OTHER PUBLICATIONS

Ragsdale, Life with Carbon Monoxide; Critical Reviews in Biochemistry and Molecular Biology, (2004) 39:165-195.

Reid, et al., Transformation of Clostridium Acetobutylicum Protoplasts with Bacteriophage DNA; Applied & Environmental Microbioloty, (1983), 45:305-307.

Rothstein, Clostridium thermosaccharolyticum Strain Deficient in Acetate production; Journal of Bacteriology, (1986) 165:319-320.

Sipma, et al., Microbial CO Conversions with Applications in Synthesis Gas Purification and Bio-Desulfurization; critical reviews in Biotechnology, (2006) 2641-2665.

Tanner, et al., Acetogenic Species ill Clostridial rRNA Homology group I, International Journal of Systematic Bacteriology, (1993) 43:232-236.

Tyurin, et al., Electransformation of Clostridium thermocellum; Applied and Environmental Microbiology, (2004) 70:883-890.

Vega, et al., The Biological Production of Ethanol from Synthesis gas; Applied Biochemistry and Biotechnology, 20-21:781-797.

Weisblum, et al., Plasmid Copy Number Control: Isolation and Characterization of High-Copy-Number Mutants of Plasmid pE194; Journal of Bacteriology, (1979) 137:635-643.

Williams, et al., Conjugative Plasmid Transfer from *Escherichia coli* to *Costridium acetobutylicum*; Journal of General Microbioloty (1990), 136:819-826.

Young, et al., 6 Genetic methods in Clostridia; Methods in Microbiology, (1999) 29:191-207.

Henstra, et al., Microbiology of synthesis gas fermentation for biofuel production, Current Opinion in Biotechnology, Jun. 8, 2007, vol. 18, No. 3, pp. 200-206.

European Search Report for App. No. EP 10853023.9, mailed Dec. 2, 2013.

\* cited by examiner

```
                 ********  *  *:.******..:*.***:.****:.****.**************.*:*.************:.**********.**.**  ****
C. ragsdalei     MKGFAMLGI NKLGWI EKKNPVPGPYDAI VHPLAVSPCTSDI HTVFEGALGNRENM LGHEAVGEI AEVGSEVKDFKVGDRVI VPCTTPDW
C. ljungdahlii   MKGFAMLGI NKLGWI EKKNPVPGPYDAI VHPLAVSPCTSDI HTVFEGALGNRENM LGHEAVGEI AEVGSEVKDFKVGDRVI VPCTTPDW
T. ethanolicus   MKGFAMLSI GKVGWI EKEKPAPGPFDAI VRPLAVAPCTSDI HTVFEGAI GERHNM LGHEAVGEVVEVGSEVKDFKPGDRVVVPAI TPDW :  ***  *:. *. *******  *. ;;. ******.  ***.  *;.*****************:*: .*. :.*.*
C. ragsdalei     RSLEVQAGFQQHSNGMLAGWKFSNFKDGVFADYFHVNDADMNLAI LPDEI PLESAVMMTDMVTTGFHGAELADI KMGSSVVVI GI GAVGL
C. ljungdahlii   RSLEVQAGFQQHSNGMLAGWKFSNFKDGVFADYFHVNDADMNLAI LPDEI PLESAVMMTDMVTTGFHGAELADI KMGSSVVVI GI GAVGL
T. ethanolicus   VTSEVQRGYHQHSGGMLAGWKFSNVKDGVFGEFFHVNDADMNLAHLPKEI PLEAAVMPDMVTTGFHGAELADI ELGATVAVLGI GPVGL :   *.  .******  *******.;;..**********.*  *  *..*****  *.***  *: . *  .***.*.*.**.*
C. ragsdalei     NGI AGSKLRGAGRI I GVGSRPVEVETAKFYGATDI VNYKNGD VEQI MDLTHGKGVDRVI MAGGGAETLAQAVTMVKPGGVI SNI NYHGS
C. ljungdahlii   NGI AGSKLRGAGRI I GVGSRPVCVETAKFYGATDI VNYKNGD VEQI MDLTHGKGVDRVI MAGGGAETLAQAVTMVKPGGVI SNI NYHGS
T. ethanolicus   NAVAGAKLRGAGRI I AVGSRPVGVDAAKYYGATDI VNYKDGPI ESGI MNLTEGKGVDAAI I AGGNADI NATAVKI VKPGGTI ANVNYFGE

*:. **. **:. ************. ***********  *  ****. **  *. ****** ;. ****** . ****. *** . *******  **
C. ragsdalei     GDTLPI PRVQMGCGVAHKTI RGGLCPGGRLRMEML RDLVLYKRVDLSKLVTHVFDGAENI EKALLLMKNKPKDLI KSVVTF-
C. ljungdahlii   GDTLPI PRVQVGCGVAHKTI RGGLCPGGRLRMEML RDLVLYKRVDLSKLVTHVFDGAENI EKALLLMKNKPKDLI KSVVTF-
T. ethanolicus   GEVLPVPRLEVGCCGVAHKTI KGGLCPGGRLRMERLI DLVFYKPVDPSKLVTHVFQGFDNI EKAFMLMKDKPKDLI KPVVI LA
```

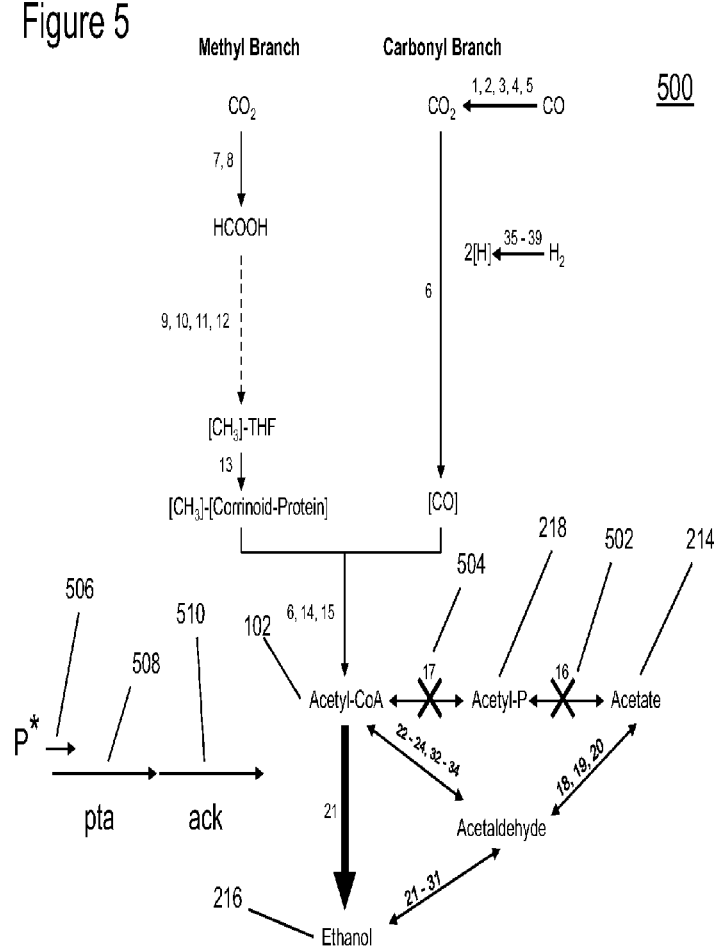

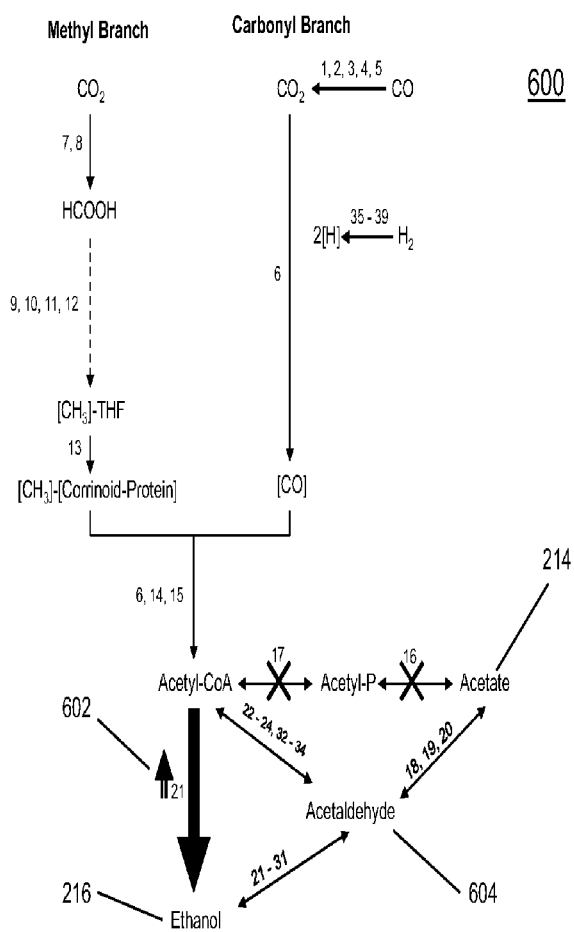

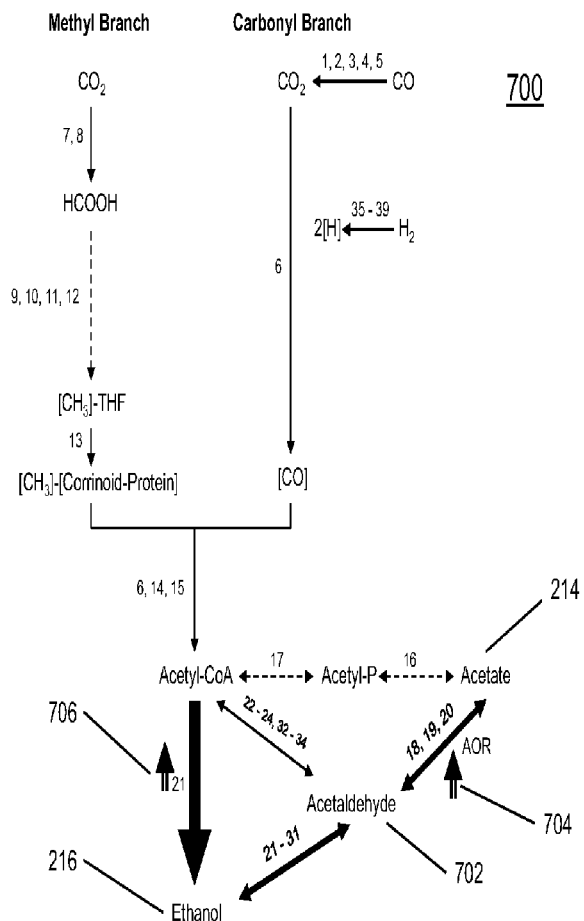

SEQUENCE LISTING

```
<160> NUMBER OF SEQ ID NOS: 6

<210> SEQ ID NO 1
<211> LENGTH: 3899
<212> TYPE: DNA
<213> ORGANISM: Clostridium ragsdalei

<400> SEQUENCE: 1
tattatatca  atatagaata  attttcaatc  aaataagaat  tattttatat  tttatattga       60
caaggaaacc  gaaaaggttt  atattattgt  tattggataa  caattatttt  ttagttagtt      120
gtacttgtaa  ataaatagta  ttaattaata  ctattaaact  attacagttt  ttgattctta      180
gtataagtat  tcttagtatc  tttagcactt  agaatacgtt  atcctttagg  agaataatcc      240
taatcagtaa  ttttaataat  ttaatagtat  acttaaatag  tatagtttgg  aggttttatt      300
atgtcaaata  acaaaatttg  taagtcagca  gataaggtac  ttgaaaagtt  tataggttct      360
ctagatggtg  tagaaacttc  tcatcatagg  gtagaaagcc  aaagtgttaa  atgtggtttt      420
ggtcagctag  gagtctgctg  tagactctgt  gcaaacggtc  cctgcagaat  aacacctaaa      480
```

```
gctccaagag gagtatgtgg tgctagtgct gataccatgg ttgcaagaaa ctttcttaga    540
gctgtagctg ccggcagtgg atgttatatc catatagtcg aaaatacagc tagaaacgta    600
aaatcagtag gtgaaaccgg cggagagata aaaggaatga atgctctcaa caccctagca    660
gaaaaacttg gtataacaga atctgaccca cataaaaaag ctgtactagt agctgtgccg    720
tattaaagga cttatacaaa ccaaaattcg aaaaaatgga agttataaat aaattagctt    780
atgcacctag actagaaaat tggaacaaat taaatataat gcctggcggt gcaaaatcag    840
aagttttga tggtgtagta aaaacttcta caaatctaaa cagcgaccct gtagatatgc    900
ttctaaattg tttaaaactt ggaatatcca ctgggattta cggacttacc cttacaaatt    960
tattaaatga cataatttta ggtgaacctg ctataagacc tgcaaaagtt ggttttaaag   1020
ttgtagatac ggattatata aatttgatga taacaggcca ccagcactcc atgattgccc   1080
accttcaaga agaacttgta aaacctgaag ctgtaaaaaa agcccaagca gttggtgcta   1140
aaggattcaa actagttgga tgtacctgtg tcggacagga tttacagtta agaggtaaat   1200
actatactga tgttttctcc ggtcatgcag gaaataactt tacaagtgaa gccttaatag   1260
caactggagg tatagatgca atagtatctg aatttaactg tactcttcct ggcatcgagc   1320
caatagctga taagttcatg gttaaaatga tatgcctaga tgacgtttct aaaaaatcaa   1380
atgcagaata tgtagaatac tcttttaaag atagagaaaa aataagcaac catgttatag   1440
atacggctat tgaaagttat aaggaaagaa gatctaaagt tacaatgaat attcctaaaa   1500
accatggctt tgatgacgtc ataacaggtg taagtgaagg ttccttaaaa tccttcttag   1560
gcggaagttg gaaacctctt gtagacttaa ttgctgctgg aaaaattaaa ggtgttgctg   1620
gaatagtagg ttgttcaaac ttaactgcca aaggtcacga tgtatttaca gtagaactta   1680
caaaagaact cataaagaga aatataattg tactttctgc aggttgttca agtggtggac   1740
ttgaaaatgt aggacttatg tctccaggag ctgctgaact tgcaggagat agcttaaaag   1800
aagtatgtaa gagcctaggt ataccacctg tactaaattt tggtccatgt cttgctattg   1860
gaagattgga aattgtagca aaagaactag cagaatacct aaaaatagat attccacagc   1920
ttccacttgt gctttctgca cctcaatggc ttgaagaaca agcattggca gatggaagtt   1980
ttggtcttgc ccttggatta ccacttcacc ttgctatatc tccttttcatt ggtggaagca   2040
aagtggtaac aaaagtttta tgtgaagata tggaaatct aacaggcggc aagcttataa   2100
tagaagacga tgtaataaaa gctgcagata aattagaaga aaccatactt gcaagaagga   2160
aaagcttagg tcttaattaa atgaaaagaa taatgataaa taaggattta tgtaccggat   2220
gcttaaattg tactttagct tgtatggcag aacacaatga aaatgggaaa tctttttatg   2280
atctggatct cagcaataaa tttcttgaaa gtagaaatca tatatctaaa gatgataatg   2340
gaaacaagct tcctatattt tgccgtcact gtgacgaacc tgagtgcgta atgacatgta   2400
tgagcggtgc catgactaaa gatcctgaaa ctggtatagt atcctatgat gagcataaat   2460
gtgccagctg ctttatgtgc gtcatgtcct gtccttatgg agtattgaaa ccagatactc   2520
agaccaaaag taaagtagtt aaatgtgacc tgtgtggtga cagagataca cctagatgcg   2580
ttgaaaattg tccaacagaa gcaatttata ttgaaaagga ggcagatctc ctatgaatga   2640
gtggtttaac aataaaaata ttttttcaca caaaatatgt aataatagga gccagtgctg   2700
ctggaataaa tgctgctaaa actttaagaa agttagataa atcctccaaa ataactatta   2760
tttcaaagga tgatgcagtt tattcaagat gtatactcca caaagtactt gagggaagta   2820
gaaatttaga taccataaat tttgtagatt ctgatttctt tgaaaaaaat aatatagaat   2880
```

```
ggataaaaga tgcagatgta agcaatattg atattgacaa gaaaaaagtc ttacttcaag   2940
acaacagcag cttcaaattt gacaagctcc ttatagcttc tggtgcttcc tcctttattc   3000
ccccagttaa aaaattaaga gaagctaaag gagtgtactc ccttagaaat tttgaagatg   3060
taactgctat acaagacaaa cttaaaaacg caaaacaagt ggtaatactt ggtgcaggtc   3120
ttgtaggaat tgatgcactt ttaggtctta tggtgaaaaa tataaagatt tcagttgtag   3180
aaatgggaga taggattctc cccttcaac tggacaaaac tgcatccact atatatgaaa   3240
agttgttaaa agaaaaaggt atagatgtct ttacttcagt taaattggaa gaggtagttt   3300
taaataaaga cggaactgta agtaaagcag tactatcaaa ttcaacttct atagattgcg   3360
atatgataat agttgctgct ggtgttagac caaatgtaag ctttataaaa gacagcagga   3420
taaaagttga aaaaggcatt gtcatagaca aacattgtaa aaccactgta gataatatat   3480
atgctgcagg agatgttact tttactgctc ctatatggcc tatagctgta aagcagggaa   3540
taactgctgc ttacaacatg gtaggtataa atagagaatt acatgacact tttggcatga   3600
agaactcaat gaatttattt aaccttccat gcgtatccct tggtaatgta aatatagcag   3660
atgaaagtta tgctgttgat acattagaag gagatggagt ttatcaaaaa atagttcaca   3720
aagatggagt aatctacggt gcacttctag ttggagatat atcttactgc ggcgtactag   3780
gatatctcat aaaaaataaa gtaaatataa gcaatatcca taaaaatatt tttgacatag   3840
attattctga tttttacaat gttgaagaag atggacaata tagttatcaa ttgaggtaa    3899
```

<210> SEQ ID NO 2
<211> LENGTH: 2506
<212> TYPE: DNA
<213> ORGANISM: Clostridium ragsdalei

<400> SEQUENCE: 2

```
gcatactgat tgattattta tttgaaaatg cctaagtaaa atatatacat attataacaa     60
taaaataagt attagtgtag gatttttaaa tagagtatct attttcagat taaattttta    120
cttatttgat ttacattgta taatattgag taaagtattg actagtaaaa ttttgtgata    180
ctttaatctg tgaaatttct tagcaaaagt tatatttttg aataattttt attgaaaaat    240
acaactaaaa aggattatag tataagtgtg tgtaattttg tgttaaattt aaagggagga    300
aataaacatg aaattgatgg aaaaaatttg gaataaggca aaggaagaca aaaaaaagat    360
tgtcttagct gaaggagaag aagaaagaac tcttcaagct tgtgaaaaaa taattaaaga    420
aggtattgca aatttaatcc ttgtagggaa tgaaaaggta atagaggaga aggcatcaaa    480
attaggcgta agtttaaatg gagcagaaat agtagatcca gaaacctcgg ataaactaaa    540
aaaatatgca gatgcttttt atgaattgag aaagaagaag ggaataacac cagaaaaagc    600
ggataaaata gtaagagatc caatatattt tgctacgatg atggttaagc ttggagatgc    660
agatggattg gtttcaggtg cagtgcatac tacaggtgat cttttgagac caggacttca    720
aatagtaaag acagctccag gtacatcagt agtttccagc acatttataa tggaagtacc    780
aaattgtgaa tatggtgaca atggtgtact tctatttgct gattgtgctg taaatccatg    840
cccagatagt gatcaattgg cttcaattgc aataagtaca gcagaaactg caaagaactt    900
atgtggaatg gatccaaaag tagcaatgct ttcattttct actaagggaa gtgcaaaaca    960
cgaattagta gataaagtta gaaatgctgt agaaattgcc aaaaaagcta aaccagattt   1020
aagtttggac ggagaattac aattagatgc ctctatcgta gaaaaggttg caagtttaaa   1080
```

```
ggctcctgaa agtgaagtag caggaaaagc aaatgtactt gtatttccag atctccaagc    1140
aggaaatata ggttataaac ttgttcaaag atttgcaaaa gctgatgcta taggacctgt    1200
atgccaggga tttgcaaaac ctataaatga tttgtcaaga ggatgtaact ccgatgatat    1260
agtaaatgta gtagctgtaa cagcagttca ggcacaagct caaaagtaaa tgaaaatatt    1320
agtagtaaac tgtggaagtt catctttaaa atatcaactt attgatatga agatgaaag    1380 cgttgtggca aaaggacttg tagaaagaat aggagcagaa ggttcagttt taacacataa    1440
agttaacgga gaaaagtttg ttacagagca gccaatggaa gatcataaag ttgctataca    1500
attagtatta aatgctcttg tagataaaaa acatggtgta ataaaagata tgtcagaaat    1560
atctgctgta gggcatagag ttttgcatgg tggaaaaaaa tatgcggcat ccattcttat    1620
tgatgacaat gtaatgaaag caatagaaga atgtattcca ttaggaccat acataatcc    1680 agctaatata atgggaatag atgcttgtaa aaaactaatg ccaaatactc caatggtagc    1740
agtatttgat acagcatttc atcagacaat gccagattat gcttatactt atgcaatacc    1800
ttatgatata tctgaaaagt atgatatcag aaaatatggt tttcatggaa cttctcatag    1860
attcgtttca attgaagcag ccaagttgtt aaagaaagat ccaaaagatc ttaagctaat    1920
aacttgtcat ttaggaaatg gagctagtat atgtgcagta aaccagggaa aagcagtaga    1980
tacaactatg ggacttactc cccttgcagg acttgtaatg ggaactagat gtggtgatat    2040
agatccagct ataataccat ttgtaatgaa agaacaggt atgtctgtag atgaaatgga    2100
tactttaatg aacaaaaagt caggaatact tggagtatca ggagtaagca gcgattttag    2160
agatgtagaa gaagctgcaa attcaggaaa tgatagagca aaacttgcat taaatatgta    2220
ttatcacaaa gttaaatctt tcataggagc ttatgttgca gttttaaatg gagcagatgc    2280
tataatattt acagcaggac ttggagaaaa ttcagctact agcagatctg ctatatgtaa    2340
gggattaagc tattttggaa ttaaaataga tgaagaaaag aataagaaaa ggggagaagc    2400
actagaaata agcacacctg attcaaagat aaaagtatta gtaattccta caaatgaaga    2460
acttatgata gctagggata caaaagaaat agttgaaaat aaataa                  2506
```

<210> SEQ ID NO 3
<211> LENGTH: 1056
<212> TYPE: DNA
<213> ORGANISM: Clostridium ragsdalei

<400> SEQUENCE: 3

```
atgaaaggtt ttgcaatgtt aggtattaac aagttaggat ggattgaaaa gaaaaaccca     60
gtaccaggtc cttatgatgc gattgtacat cctctagctg tatccccatg tacatcagat    120
atacatacgg tttttgaagg agcacttggt aataggaaa atatgatttt aggtcacgaa    180
gctgtaggtg aaatagctga agttggcagt gaagttaaag attttaaagt tggcgataga    240
gttatcgtac catgcacaac acctgactgg agatccttag aagtccaagc tggttttcaa    300
cagcattcaa acggtatgct tgcaggatgg aagttttcca attttaaaga cggtgtattt    360
gcagattact ttcatgtaaa cgatgcagat atgaatcttg caatacttcc agatgaaata    420
cctttagaaa gtgcagttat gatgacagac atgatgacta ctggttttca tggggcagaa    480
cttgctgaca taaaaatggg ttccagtgtt gtcgtaattg gtataggagc tgttggatta    540
atgggaatag ccggttccaa acttcgagga gcaggtagaa ttatcggtgt tggaagcaga    600
cccgtttgtg ttgaaacagc taaatttat ggagcaactg atattgtaaa ttataaaaat    660
ggtgatatag ttgaacaaat aatggactta actcatggta aaggtgtaga ccgtgtaatc    720
```

```
atggcaggcg gtggtgctga aacactagca caagcagtaa ctatggttaa acctggcggc    780
gtaatttcta acatcaacta ccatggaagc ggtgatactt tgccaatacc tcgtgttcaa    840
tggggctgcg gcatggctca aaaactata  agaggagggt tatgtcccgg cggacgtctt    900
agaatggaaa tgctaagaga ccttgttcta tataaacgtg ttgatttgag caaacttgtt    960
actcatgtat ttgatggtgc agaaaatatt gaaaaggccc ttttgcttat gaaaaataag   1020
ccaaaagatt taattaaatc agtagttaca ttctaa                            1056
```

<210> SEQ ID NO 4
<211> LENGTH: 351
<212> TYPE: PRT
<213> ORGANISM: Clostridium ragsdalei

<400> SEQUENCE: 4

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
```

```
                    305                 310                 315                 320
Thr His Val Phe Asp Gly Ala Glu Asn Ile Glu Lys Ala Leu Leu Leu
                    325                 330                 335
Met Lys Asn Lys Pro Lys Asp Leu Ile Lys Ser Val Val Thr Phe
                340                 345                 350

<210> SEQ ID NO 5
<211> LENGTH: 351
<212> TYPE: PRT
<213> ORGANISM: Clostridium ljungdahlii

<400> SEQUENCE: 5

Met Lys Gly Phe Ala Met Leu Gly Ile Asn Lys Leu Gly Trp Ile Glu
1               5                   10                  15
Lys Lys Asn Pro Val Pro Gly Pro Tyr Asp Ala Ile Val His Pro Leu
                20                  25                  30
Ala Val Ser Pro Cys Thr Ser Asp Ile His Thr Val Phe Glu Gly Ala
                35                  40                  45
Leu Gly Asn Arg Glu Asn Met Ile Leu Gly His Glu Ala Val Gly Glu
        50                  55                  60
Ile Ala Glu Val Gly Ser Glu Val Lys Asp Phe Lys Val Gly Asp Arg
65                  70                  75                  80
Val Ile Val Pro Cys Thr Thr Pro Asp Trp Arg Ser Leu Glu Val Gln
                85                  90                  95
Ala Gly Phe Gln Gln His Ser Asn Gly Met Leu Ala Gly Trp Lys Phe
                100                 105                 110
Ser Asn Phe Lys Asp Gly Val Phe Ala Asp Tyr Phe His Val Asn Asp
                115                 120                 125
Ala Asp Met Asn Leu Ala Ile Leu Pro Asp Glu Ile Pro Leu Glu Ser
        130                 135                 140
Ala Val Met Met Thr Asp Met Met Thr Thr Gly Phe His Gly Ala Glu
145                 150                 155                 160
Leu Ala Asp Ile Lys Met Gly Ser Ser Val Val Ile Gly Ile Gly
                165                 170                 175
Ala Val Gly Leu Met Gly Ile Ala Gly Ser Lys Leu Arg Gly Ala Gly
                180                 185                 190
Arg Ile Ile Gly Val Gly Ser Arg Pro Val Cys Val Glu Thr Ala Lys
                195                 200                 205
Phe Tyr Gly Ala Thr Asp Ile Val Asn Tyr Lys Asn Gly Asp Ile Val
        210                 215                 220
Glu Gln Ile Met Asp Leu Thr His Gly Lys Gly Val Asp Arg Val Ile
225                 230                 235                 240
Met Ala Gly Gly Gly Ala Glu Thr Leu Ala Gln Ala Val Thr Met Val
                245                 250                 255
Lys Pro Gly Gly Val Ile Ser Asn Ile Asn Tyr His Gly Ser Gly Asp
                260                 265                 270
Thr Leu Pro Ile Pro Arg Val Gln Trp Gly Cys Gly Met Ala His Lys
                275                 280                 285
Thr Ile Arg Gly Gly Leu Cys Pro Gly Gly Arg Leu Arg Met Glu Met
                290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                325                 330                 335
```

```
Met Lys Asn Lys Pro Lys Asp Leu Ile Lys Ser Val Val Thr Phe
                340                 345                 350

<210> SEQ ID NO 6
<211> LENGTH: 352
<212> TYPE: PRT
<213> ORGANISM: Thermoanaerobacter ethanolicus

<400> SEQUENCE: 6

Met Lys Gly Phe Ala Met Leu Ser Ile Gly Lys Val Gly Trp Ile Glu
  1               5                  10                  15

Lys Glu Lys Pro Ala Pro Gly Pro Phe Asp Ala Ile Val Arg Pro Leu
                 20                  25                  30

Ala Val Ala Pro Cys Thr Ser Asp Ile His Thr Val Phe Glu Gly Ala
             35                  40                  45

Ile Gly Glu Arg His Asn Met Ile Leu Gly His Glu Ala Val Gly Glu
 50                  55                  60

Val Val Glu Val Gly Ser Glu Val Lys Asp Phe Lys Pro Gly Asp Arg
 65                  70                  75                  80

Val Val Val Pro Ala Ile Thr Pro Asp Trp Trp Thr Ser Glu Val Gln
                 85                  90                  95

Arg Gly Tyr His Gln His Ser Gly Gly Met Leu Ala Gly Trp Lys Phe
                100                 105                 110

Ser Asn Val Lys Asp Gly Val Phe Gly Glu Phe Phe His Val Asn Asp
            115                 120                 125

Ala Asp Met Asn Leu Ala His Leu Pro Lys Glu Ile Pro Leu Glu Ala
        130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
290                 295                 300

Leu Ile Asp Leu Val Phe Tyr Lys Pro Val Asp Pro Ser Lys Leu Val
305                 310                 315                 320

Thr His Val Phe Gln Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350
```

GENES ENCODING KEY CATALYZING MECHANISMS FOR ETHANOL PRODUCTION FROM SYNGAS FERMENTATION

RELATED U.S. APPLICATION DATA

This application claims the benefit of and priority to U.S. Pat. No. 8,628,943 filed Jun. 9, 2010 as a divisional which claims the benefit of and priority to U.S. Pat. No. 8,039,239 filed Dec. 16, 2008 as a continuation-in-part application. The entirety of these applications are incorporated by reference herein. The content of the sequence listing information recorded in computer readable form is identical to the compact disc sequence listing and, where applicable, includes no new matter, as required by 37 CFR 1.821 (e), 1.821(f), 1.821 (g), 1.825(b), or 1.825(d).

FIELD OF THE INVENTION

This invention relates to the cloning and expression of novel genetic sequences of microorganisms used in the biological conversion of CO, H2, and mixtures comprising CO and/or H2 to biofuel products.

BACKGROUND

Synthetic gas (syngas) is a mixture of carbon monoxide (CO) gas, carbon dioxide ($CO_2$) gas, and hydrogen ($H_2$) gas, and other volatile gases such as $CH_4$, $N_2$, $NH_3$, $H_2S$ and other trace gases. Syngas is produced by gasification of various organic materials including biomass, organic waste, coal, petroleum, plastics, or other carbon containing materials, or reformed natural gas.

Acetogenic Clostridia microorganisms grown in an atmosphere containing syngas are capable of absorbing the syngas components CO, $CO_2$, and $H_2$ and producing aliphatic $C_2$-$C_6$ alcohols and aliphatic $C_2$-$C_6$ organic acids. These syngas components activate Wood-Ljungdahl metabolic pathway 100, shown in FIG. 1, which leads to the formation of acetyl coenzyme A 102, a key intermediate in the pathway. The enzymes activating Wood-Ljungdahl pathway 100 are carbon monoxide dehydrogenase (CODH) 104 and hydrogenase ($H_2$ase) 106. These enzymes capture the electrons from the CO and $H_2$ in the syngas and transfer them to ferredoxin 108, an iron-sulfur (FeS) electron carrier protein. Ferredoxin 108 is the main electron carrier in Wood-Ljungdahl pathway 100 in acetogenic Clostridia, primarily because the redox potential during syngas fermentation is very low (usually between −400 and −500 mV). Upon electron transfer, ferredoxin 108 changes its electronic state from $Fe^{3+}$ to $Fe^{2+}$. Ferredoxin-bound electrons are then transferred to cofactors $NAD^+$ 110 and $NADP^+$ 112 through the activity of ferredoxin oxidoreductases 114 (FORs). The reduced nucleotide cofactors ($NAD^+$ and $NADP^+$) are used for the generation of intermediate compounds in Wood-Ljungdahl pathway 100 leading to acetyl-CoA 102 formation.

Acetyl-CoA 102 formation through Wood-Ljungdahl pathway 100 is shown in greater detail in FIG. 2. Either $CO_2$ 202 or CO 208 provide substrates for the pathway. The carbon from $CO_2$ 202 is reduced to a methyl group through successive reductions first to formate, by formate dehydrogenase (FDH) enzyme 204, and then is further reduced to methyl tetrahydrofolate intermediate 206. The carbon from CO 208 is reduced to carbonyl group 210 by carbon monoxide dehydrogenase (CODH) 104 through a second branch of the pathway. The two carbon moieties are then condensed to acetyl-CoA 102 through the action of acetyl-CoA synthase (ACS) 212, which is part of a carbon monoxide dehydrogenase (CODH/ACS) complex. Acetyl-CoA 102 is the central metabolite in the production of $C_2$-$C_6$ alcohols and acids in acetogenic Clostridia.

Ethanol production from Acetyl CoA 102 is achieved via one of two possible paths. Aldehyde dehydrogenase facilitates the production of acetaldehyde, which is then reduced to ethanol by the action of primary alcohol dehydrogenases. In the alternative, in homoacetogenic microorganisms, an NADPH-dependent acetyl CoA reductase ("AR") facilitates the production of ethanol directly from acetyl CoA.

Wood-Ljungdahl pathway 100 is neutral with respect to ATP production when acetate 214 is produced (FIG. 2). When ethanol 216 is produced, one ATP is consumed in a step involving the reduction of methylene tetrahydrafolate to methyl tetrahydrofolate 206 by a reductase, and the process is therefore net negative by one ATP. The pathway is balanced when acetyl-$PO_4$ 218 is converted to acetate 214.

Acetogenic Clostridia organisms generate cellular energy by ion gradient-driven phosphorylation. When grown in a CO atmosphere, a transmembrane electrical potential is generated and used to synthesize ATP from ADP. Enzymes mediating the process include hydrogenase, NADH dehydrogenases, carbon monoxide dehydrogenase, and methylene tetrahydrofolate reductase. Membrane carriers that have been shown to be likely involved in the ATP generation steps include quinone, menaquinone, and cytochromes.

The acetogenic Clostridia produce a mixture of $C_2$-$C_6$ alcohols and acids, such as ethanol, n-butanol, hexanol, acetic acid, and butyric acid, that are of commercial interest through Wood-Ljungdahl pathway 100. For example, acetate and ethanol are produced by *C. ragsdalei* in variable proportions depending in part on fermentation conditions. However, the cost of producing the desired product, an alcohol such as ethanol, for example, can be lowered significantly if the production is maximized by reducing or eliminating production of the corresponding acid, in this example acetate. It is therefore desirable to metabolically engineer acetogenic Clostridia for improved production of selected $C_2$-$C_6$ alcohols or acids through Wood-Ljungdahl pathway 100 by modulating enzymatic activities of key enzymes in the pathway.

SUMMARY OF THE INVENTION

One aspect of the present invention provides novel sequences for three key operons which code for enzymes that catalyze the syngas to ethanol metabolic process: one coding for a carbon monoxide dehydrogenase, a membrane-associated electron transfer protein, a ferredoxin oxidoreductase, and a promoter; a second operon coding for an acetate kinase, phosphotransacetylase, and a promoter, and a third operon coding for an acetyl CoA reductase and a promoter.

Another aspect of the invention provides an isolated vector or transformant containing the polynucleotide sequence coding for the operons described above.

Another aspect of the invention provides a method of producing ethanol comprising: isolating and purifying anaerobic, ethanologenic microorganisms carrying the polynucleotides coding for an operon comprising carbon monoxide dehydrogenase, a membrane-associated electron transfer protein, a ferredoxin oxidoreductase, and a promoter; an operon coding for an acetate kinase, phosphotransacetylase, and a promoter, or an operon coding for an acetyl CoA reductase and a promoter; fermenting syngas with said microorganisms in a fermentation bioreactor; providing sufficient growth conditions for cellular production of NADPH, including but not limited to sufficient zinc, to facilitate ethanol production from acetyl CoA.

Another aspect of the invention provides a method of producing ethanol by isolating and purifying anaerobic, ethanologenic microorganisms carrying the polynucleotide coding for acetyl coenzyme A reductase; fermenting syngas with said microorganisms in a fermentation bioreactor; and providing sufficient growth conditions for cellular production of NADPH, including but not limited to sufficient zinc, to facilitate ethanol production from acetyl CoA.

Yet another aspect of the present invention provides a method of increasing ethanologenesis or the ethanol to acetate production ratio in a microorganism containing the nucleotide sequence(s) coding for one of more of the operons described above, said method comprising: modifying, duplicating, or downregulating a promoter region of said nucleotide sequence to increase the activity of the Acetyl Coenzyme A reductase said sequence being at least 98% identical to SEQ ID NO. 3, or to cause overexpression or underexpression of the nucleotide sequence.

The present invention is illustrated by the accompanying figures portraying various embodiments and the detailed description given below. The figures should not be taken to limit the invention to the specific embodiments, but are for explanation and understanding. The detailed description and figures are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying figures.

BRIEF DESCRIPTION OF THE DRAWINGS

FIG. 4 is a diagram showing the amino acid alignment of the gene for NADPH dependent secondary alcohol dehydrogenase in *C. ragsdalei* [SEQ ID No. 4], *C. ljungdahlii* [SEQ ID No. 5] and *Thermoanaerobactor ethanolicus* [SEQ ID No. 6], in accordance with the invention;

FIG. 5 is a diagram illustrating the Wood-Ljungdahl pathway for ethanol synthesis and showing a strategy for specifically attenuating or eliminating acetate production in acetogenic Clostridia by knocking out the genes encoding acetate kinase (ack) and phosphotransacetylase (pta) or by modulating acetate production by mutating or replacing the promoter driving phosphotransacetylase and acetate kinase gene expression, in accordance with the invention;

FIG. 6 is a diagram of the Wood-Ljungdahl pathway for ethanol synthesis, and shows a strategy for specifically increasing ethanol production in *C. ragsdalei* by overexpression of an acetyl CoA reductase in a host knocked out for acetate kinase or phosphotransacetylase activity, in accordance with the invention;

FIG. 7 is a diagram of the Wood-Ljungdahl pathway for ethanol synthesis, and showing a strategy for increasing ethanol production in acetogenic Clostridia by aldehyde ferredoxin oxidoreductase (AOR) in a host strain that is attenuated in its ability to produce acetate and has increased NADPH-dependent alcohol dehydrogenase activity, in accordance with the invention;

DETAILED DESCRIPTION

The present invention is directed to novel genetic sequences coding for acetogenic Clostridia micro-organisms that produce ethanol and acids from syngas comprising CO, $CO_2$, $H_2$, or mixtures thereof.

Several species of acetogenic Clostridia that produce $C_2$-$C_6$ alcohols and acids via the Wood-Ljungdahl pathway have been characterized: *C. ragsdalei, C. ljungdahlii, C. carboxydivorans*, and *C. autoethanogenum*. The genomes of three of these microorganisms were sequenced in order to locate and modify the portions of the genome that code for the enzymes of interest.

Figure 1:
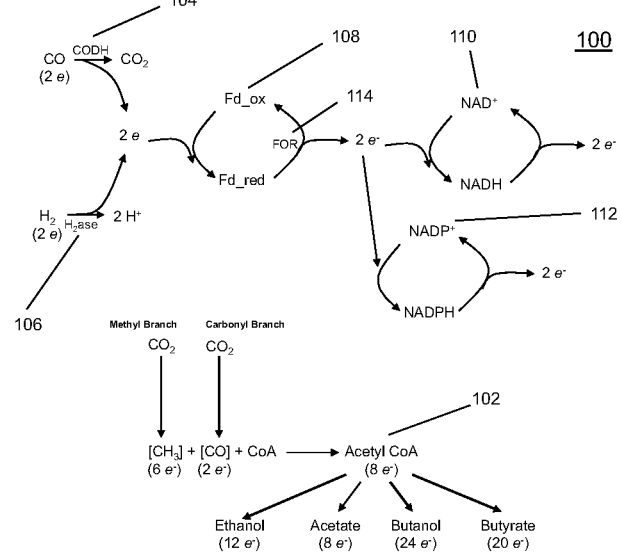
FIG. 1 is a diagram illustrating the electron flow pathway during syngas fermentation in acetogenic Clostridia including some of the key enzymes involved in the process.
Figure 2:
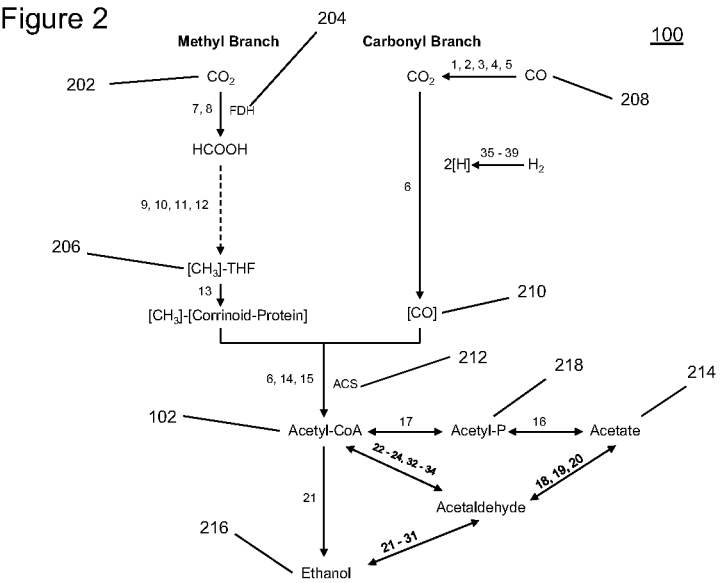
FIG. 2 is a diagram illustrating the Wood-Ljungdahl ($C_1$) pathway for acetylCoA production and the enzymatic conversion of acetyl-CoA to acetate and ethanol.

The genes that code for enzymes in the Wood-Ljungdahl metabolic pathway and ethanol synthesis identified in the *C. ragsdalei* genome are presented in Table 1. The first column identifies the pathway associated with each gene. The gene identification numbers indicated in the second column correspond to the numbers representing the enzymes involved in the metabolic reactions in the Wood-Ljungdahl pathway shown in FIG. 1 and FIG. 2.

TABLE 1

*Clostridium ragsdalei* genes used in metabolic engineering experiments.

| Pathway | Gene ID | Gene Name | EC number | ORF ID | Copy ID | Description |
|---|---|---|---|---|---|---|
| Wood-Ljungdahl | 1 | Carbon Monoxide Dehydrogenase | 1.2.2.4 | RCCC00183 | CODH_1 | CO oxidation |
|  | 2 |  |  | RCCC01175 | CODH_2 | CO oxidation |
|  | 3 |  |  | RCCC01176 | CODH_3 | CO oxidation |
|  | 4 |  |  | RCCC02026 | CODH_4 | CO oxidation |
|  | 5 |  |  | RCCC03874 | CODH_5 | CO oxidation |
|  | 6 | Carbon Monoxide Dehydrogenase/Acetyl-CoA Synthase | 1.2.99.2 | RCCC03862 | cooS/acsA | bifunctional CODH/ACS enzyme, carbon fixation |
|  | 7 | Formate Dehydrogenase | 1.2.1.2 | RCCC00874 | FDH_1 | Methyl branch carbon fixation |
|  | 8 |  |  | RCCC03324 | FDH_2 | carbon fixation |

TABLE 1-continued

*Clostridium ragsdalei* genes used in metabolic engineering experiments.

| Pathway | Gene ID | Gene Name | EC number | ORF ID | Copy ID | Description |
|---|---|---|---|---|---|---|
| | 9 | Formyltetrahydrofolate Synthase | 6.3.4.3 | RCCC03872 | FTHFS | Methyl branch carbon fixation |
| | 10 | Methenyltetrahydrofolate cyclohydrolase | 3.5.4.9 | RCCC03870 | MEC | Methyl branch carbon fixation |
| | 11 | Methylenetetrahydrofolate dehydrogenase | 1.5.1.5 | RCCC03870 | MED | Methyl branch carbon fixation |
| | 12 | Methylenetetrahydrofolate reductase | 1.5.1.20 | RCCC03868 | MER | Methyl branch carbon fixation |
| | 13 | Methyltransferase | 2.1.1.13 | RCCC03863 | acsE | Methyl branch carbon fixation |
| | 14 | Corrinoid/Iron-sulfur protein | 1.2.99.2 | RCCC03864 | acsC | Part of CODH/ACS complex, Large subunit |
| | 15 | Corrinoid/Iron-sulfur protein | 1.2.99.2 | RCCC03865 | acsD | Part of CODH/ACS complex, Small subunit |
| Ethanol and acetate production | 16 | Acetate Kinase | 2.7.2.1 | RCCC01717 | ACK | Acetate production |
| | 17 | Phospho-transacetylase | 2.3.1.8 | RCCC01718 | PTA | Acetate production |
| | 18 | Tungsten-containing aldehyde ferredoxin oxidoreductase | 1.2.7.5 | RCCC00020 | AOR_1 | Reduction of acetate to acetaldehyde |
| | 19 | | 1.2.7.5 | RCCC00030 | AOR_2 | Reduction of acetate to acetaldehyde |
| | 20 | | 1.2.7.5 | RCCC01183 | AOR_3 | Reduction of acetate to Acetaldehyde |
| | 21 | Acetyl-CoA Reductase | 1.1.1.2 | RCCC02715 | ADH_1 | zinc-containing, NADPH-Dependent Acetyl-CoA reductase |
| | 22 | Alcohol Dehydrogenase | 1.1.1.1 | RCCC01356 | ADH_2 | two pfam domain: FeADH and ALDH, AdhE |
| | 23 | | 1.1.1.1 | RCCC01357 | ADH_3 | two pfam domain: FeADH and ALDH, AdhE |
| | 24 | | 1.1.1.1 | RCCC01358 | ADH_4 | two pfam domain: FeADH and ALDH, AdhE, fragment (76aa) |
| | 25 | | 1.1.1.1 | RCCC03300 | ADH_5 | one pfam domain: FeADH |
| | 26 | | 1.1.1.1 | RCCC03712 | ADH_6 | one pfam domain: FeADH |
| | 27 | | 1.1.1.1 | RCCC04095 | ADH_7 | one pfam domain: FeADH |
| | 28 | | 1.—.—.— | RCCC00004 | ADH_8 | short chain ADH, multiple copy |
| | 29 | | 1.—.—.— | RCCC01567 | ADH_9 | Short chanin ADH, multiple copy |
| | 30 | | 1.—.—.— | RCCC02765 | ADH_10 | short chain ADH, multiple copy |
| | 31 | | 1.—.—.— | RCCC02240 | ADH_11 | short chain ADH, multiple copy |
| | 32 | Aldehyde Dehydrogenase | 1.2.1.10 | RCCC03290 | ALDH_1 | Acetylating |
| | 33 | | 1.2.1.10 | RCCC04101 | ALDH_2 | Acetylating |
| | 34 | | 1.2.1.10 | RCCC04114 | ALDH_3 | Acetylating |
| Hydrogenase | 35 | Hydrogenase | 1.12.7.2 | RCCC00038 | HYD_1 | Fe only, H2 production |
| | 36 | | 1.12.7.2 | RCCC00882 | HYD_2 | Fe only, large subunit, H2 production |

TABLE 1-continued

Clostridium ragsdalei genes used in metabolic engineering experiments.

| Pathway | Gene ID | Gene Name | EC number | ORF ID | Copy ID | Description |
|---|---|---|---|---|---|---|
| | 37 | | 1.12.7.2 | RCCC01252 | HYD_3 | Fe only, H2 production |
| | 38 | | 1.12.7.2 | RCCC01504 | HYD_4 | Fe only, H2 production |
| | 39 | | 1.12.7.2 | RCCC02997 | HYD_5 | Ni—Fe large subunit, H2 oxidation |
| Electron carrier | 40 | Ferredoxin | | RCCC00086 | | |
| | 41 | | | RCCC00301 | | |
| | 42 | | | RCCC00336 | | |
| | 43 | | | RCCC01168 | | |
| | 44 | | | RCCC01415 | | |
| | 45 | | | RCCC01825 | | |
| | 46 | | | RCCC02435 | | |
| | 47 | | | RCCC02890 | | |
| | 48 | | | RCCC03063 | | |
| | 49 | | | RCCC03726 | | |
| | 50 | | | RCCC04003 | | |
| | 51 | | | RCCC04147 | | |
| Electron transfer | 52 | Pyridine nucleotide-disulphide oxidoreductases | | RCCC02615 | | glutamate synthase small chain, but no large chain next to it |
| | 53 | | | RCCC02028 | | next to cooF and cooS, probably important for reduced pyridine cofactor generation |
| | 54 | | | RCCC03071 | | NADH dehydrogenase, not part of an operon |
| | 55 | Membrane-associated electron transfer FeS protein, cooF | | RCCC02027 | cooF | Between gene number 4 and gene number 53 |

Sequence analysis of the *C. ljungdahlii* genome was conducted. Genes coding for enzymes in the Wood-Ljungdahl pathway, ethanol and acetate production, and electron transfer have been identified and located within the genome. The results are presented in Table 2.

TABLE 2

Clostridium ljungdahlii genes used in metabolic engineering experiments.

| Pathway | Gene ID | Gene Name | EC number | ORF ID | Copy ID | Description |
|---|---|---|---|---|---|---|
| Wood-Ljungdahl | 1 | Carbon Monoxide Dehydrogenase | 1.2.2.4 | RCCD00983 | CODH_1 | CO oxidation |
| | 2 | | | RCCD00984 | CODH_2 | CO oxidation |
| | 3 | | | RCCD01489 | CODH_3 | CO oxidation |
| | 4 | | | RCCD04299 | CODH_4 | CO oxidation |
| | 5 | Carbon Monoxide Dehydrogenase/Acetyl-CoA Synthase | 1.2.99.2 | RCCD00972 | CODH_ACS | bifunctional CODH/ACS enzyme, carbon fixation |
| | 6 | Formate Dehydrogenase | 1.2.1.2 | RCCD01275 | FDH_1 | Methyl branch carbon fixation |
| | 7 | | | RCCD01472 | FDH_2 | Methyl branch carbon fixation |
| | 8 | Formyltetrahydrofolate Synthase | 6.3.4.3 | RCCD00982 | FTHFS | Methyl branch carbon fixation |
| | 9 | Methenyltetrahydrofolate cyclohydrolase | 3.5.4.9 | RCCD00980 | MEC | Methyl branch carbon fixation |
| | 10 | Methylenetetrahydrofolate dehydrogenase | 1.5.1.5 | RCCD00980 | MED | Methyl branch carbon fixation |
| | 11 | Methylenetetrahydrofolate reductase | 1.5.1.20 | RCCD00978 | MER | Methyl branch carbon fixation |

TABLE 2-continued

*Clostridium ljungdahlii* genes used in metabolic engineering experiments.

| Pathway | Gene ID | Gene Name | EC number | ORF ID | Copy ID | Description |
|---|---|---|---|---|---|---|
| | 12 | Methyltransferase | 2.1.1.13 | RCCD00973 | MET | Methyl branch carbon fixation |
| | 13 | Corrinoid/Iron-sulfur protein | 1.2.99.2 | RCCD00974 | COPL | Part of CODH/ACS complex, Large subunit |
| | 14 | Corrinoid/Iron-sulfur protein | 1.2.99.2 | RCCD00975 | COPS | Part of CODH/ACS complex, Small subunit |
| Ethanol and acetate production | 15 | Acetate Kinase | 2.7.2.1 | RCCD02720 | ACK | Acetate production |
| | 16 | Phospho-transacetylase | 2.3.1.8 | RCCD02719 | PTA | Acetate Production |
| | 17 | Tungsten-containing aldehyde ferredoxin oxidoreductase | 1.2.7.5 | RCCD01679 | AOR_1 | Reduction of acetate to acetaldehyde |
| | 18 | | 1.2.7.5 | RCCD01692 | AOR_2 | Reduction of acetate to acetaldehyde |
| | 19 | Acetyl-CoA Reductase | 1.1.1.2 | RCCD00257 | ADH_1 | zinc-containing, NADPH-dependent Acetyl-CoA Reductase |
| | 20 | Alcohol Dehydrogenase | 1.1.1.1 | RCCD00167 | ADH_2 | two pfam domain: FeADH and ALDH, AdhE |
| | 21 | | 1.1.1.1 | RCCD00168 | ADH_3 | two pfam domain: FeADH and ALDH, AdhE |
| | 22 | | 1.1.1.1 | RCCD02628 | ADH_5 | one pfam domain: FeADH |
| | 23 | | 1.1.1.1 | RCCD03350 | ADH_7 | one pfam domain: FeADH |
| | 24 | | 1.—.—.— | RCCD00470 | ADH_8 | short chain ADH, multiple copy |
| | 25 | | 1.—.—.— | RCCD01665 | ADH_9 | short chain ADH, multiple copy |
| | 26 | | 1.—.—.— | RCCD01767 | ADH_10 | short chain ADH, multiple copy |
| | 27 | | 1.—.—.— | RCCD02864 | ADH_11 | short chain ADH, multiple copy |
| | 28 | Aldehyde Dehydrogenase | 1.2.1.10 | RCCD02636 | ALDH_1 | Acetylating |
| | 29 | | 1.2.1.10 | RCCD03356 | ALDH_2 | Acetylating |
| | 30 | | 1.2.1.10 | RCCD03368 | ALDH_3 | Acetylating |
| Hydrogenase | 31 | Hydrogenase | 1.12.7.2 | RCCD00346 | HYD_1 | Ni—Fe large subunit, H2 oxidation |
| | 32 | | 1.12.7.2 | RCCD00938 | HYD_2 | Ni—Fe small subunit, H2 oxidation |
| | 33 | | 1.12.7.2 | RCCD01283 | HYD_3 | Fe only, large subunit, H2 production |
| | 34 | | 1.12.7.2 | RCCD01700 | HYD_4 | Fe only, H2 production |
| | 35 | | 1.12.7.2 | RCCD02918 | HYD_5 | Fe only H2 production |
| | 36 | | 1.12.7.2 | RCCD04233 | HYD_6 | Fe only, H2 production |
| Electron carrier | 37 | Ferredoxin | | RCCD00424 | | |
| | 38 | | | RCCD01226 | | |
| | 39 | | | RCCD01932 | | |
| | 40 | | | RCCD02185 | | |
| | 41 | | | RCCD02239 | | |
| | 42 | | | RCCD02268 | | |
| | 43 | | | RCCD02580 | | |
| | 44 | | | RCCD03406 | | |

TABLE 2-continued

*Clostridium ljungdahlii* genes used in metabolic engineering experiments.

| Pathway | Gene ID | Gene Name | EC number | ORF ID | Copy ID | Description |
|---|---|---|---|---|---|---|
| | 45 | | | RCCD03640 | | |
| | 46 | | | RCCD03676 | | |
| | 47 | | | RCCD04306 | | |
| Electron | 48 | Pyridine nucleotide-disulphide oxidoreductases | | RCCD00185 | | glutamate synthase small chain, but no large chain next to it |
| | 49 | | | RCCD01487 | | next to cooF and cooS, probably important for reduced pyridine cofactor generation |
| | 50 | | | RCCD00433 | | NADH dehydrogenase, not part of an operon |
| | 51 | Membrane-associated electron transfer FeS protein, cooF | | RCCD01488 | cooF | Between gene number 3 and gene number 49 |

Similarly, the genome of *C. carboxydivorans* was sequenced, and genes coding for the enzymes in the Wood-Ljungdahl pathway and ethanol and acetate synthesis were identified and located. The results are presented in Table 3.

TABLE 3

*Clostridium carboxidivorans* genes used in metabolic engineering.

| Pathway | Gene ID | Gene Name | EC Number | ORF ID | Copy ID | Description |
|---|---|---|---|---|---|---|
| Wood-Ljungdahl | 1 | Carbon Monoxide Dehydrogenase | 1.2.2.4 | RCCB04039 | CODH_1 | CO oxidation |
| | 2 | | | RCCB00154 | CODH_2 | CO oxidation |
| | 3 | | | RCCB02478 | CODH_3 | CO oxidation |
| Ethanol and acetate production | 4 | | | RCCB03963 | CODH_4 | CO oxidation |
| | 5 | | | RCCB04038 | CODH_5 | CO oxidation |
| | 6 | Carbon Monoxide Dehydrogenase/Acetyl-CoA Synthase | 1.2.99.2 | RCCB04293 | CODH_ACS | bifunctional CODH/ACS enzyme, carbon fixation |
| | 7 | Formate Dehydrogenase | 1.2.1.2 | RCCB05406 | FDH_1 | Methyl branch carbon fixation |
| | 8 | | | RCCB01346 | FDH_2 | Methyl branch carbon fixation |
| | 9 | Formyltetrahydrofolate Synthase | 6.3.4.3 | RCCB04040 | FTHFS | Methyl branch carbon fixation |
| | 10 | Methenyltetrahydrofolate cyclohydrolase | 3.5.4.9 | RCCB04042 | MEC | Methyl branch carbon fixation |
| | 11 | Methylenetetrahydrofolate dehydrogenase | 1.5.1.5 | RCCB04042 | MED | Methyl branch carbon fixation |
| | 12 | Methylenetetrahydrofolate reductase | 1.5.1.20 | RCCB04044 | MER | Methyl branch carbon fixation |
| | 13 | Methyltransferase | 2.1.1.13 | RCCB04294 | MET | Methyl branch carbon fixation |
| | 14 | Corrinoid/Iron-sulfur protein | 1.2.99.2 | RCCB04049 | COPL | Parts of CODH/ACS complex, Large subunit |
| | 15 | Corrinoid/Iron-sulfur protein | 1.2.99.2 | RCCB04047 | COPS | Part of CODH/ACS complex, Small subunit |
| | 16 | Acetate Kinase | 2.7.2.1 | RCCB05249 | ACK | Acetate production |

TABLE 3-continued

*Clostridium carboxidivorans* genes used in metabolic engineering.

| Pathway | Gene ID | Gene Name | EC Number | ORF ID | Copy ID | Description |
|---|---|---|---|---|---|---|
| | 17 | Phospho-transacetylase | 2.3.1.8 | RCCB02481 | PTA | Acetate production |
| | 18 | Tungsten-containing aldehyde ferredoxin oxidoreductase | 1.2.7.5 | RCCB00063 | AOR_1 | Reduction of acetate to acetaldehyde |
| | 19 | Alcohol Dehydrogenase | 1.1.1.2 | RCCB03584 | ADH_1 | zinc-ADH |
| | 20 | | 1.1.1.1 | RCCB03870 | ADH_2 | two pfam domain: FeADH and ALDH, AdhE |
| | 21 | | 1.1.1.1 | RCCB05675 | ADH_3 | truncated, AdhE |
| | 22 | | 1.1.1.1 | RCCB00958 | ADH_5 | one pfam domain: FeADH |
| | 23 | | 1.1.1.1 | RCCB04489 | ADH_6 | one pfam domain: FeADH |
| | 24 | | 1.1.1.1 | RCCB04503 | ADH_7 | one pfam domain: FeADH |
| | 25 | | 1.—.—.— | RCCB02465 | ADH_9 | short chain ADH, multiple copy |
| | 26 | | 1.—.—.— | RCCB05551 | ADH_10 | short chain ADH, multiple copy |
| | 27 | Aldehyde Dehydrogenase | 1.2.1.10 | RCCB02403 | ALDH_1 | Acetylating |
| | 28 | | 1.2.1.10 | RCCB02561 | ALDH_2 | Acetylating |
| | 29 | | 1.2.1.10 | RCCB04031 | ALDH_3 | Acetylating |
| Hydrogenase | 30 | Hydrogenase | 1.12.7.2 | RCCB02249 | HYD_1 | Ni—Fe large subunit, H2 oxidation |
| | 31 | | 1.12.7.2 | RCCB01319 | HYD_2 | Fe only, H2 production |
| | 32 | | 1.12.7.2 | RCCB01405 | HYD_3 | Fe only, H2 production |
| | 33 | | 1.12.7.2 | RCCB01516 | HYD_4 | Fe only, large subunit, H2 oxidation |
| | 34 | | 1.12.7.2 | RCCB03483 | HYD_5 | Fe only, H2 production |
| | 35 | | 1.12.7.2 | RCCB05411 | HYD_6 | Fe only, large subunit, H2 production |
| Electron carrier | 36 | Ferredoxin | | RCCB00234 | | |
| | 37 | | | RCCB00345 | | |
| | 38 | | | RCCB01260 | | |
| | 39 | | | RCCB01334 | | |
| | 40 | | | RCCB01775 | | |
| | 41 | | | RCCB01960 | | |
| | 42 | | | RCCB01972 | | |
| | 43 | | | RCCB02618 | | |
| | 44 | | | RCCB02638 | | |
| | 45 | | | RCCB02836 | | |
| | 46 | | | RCCB02853 | | |
| | 47 | | | RCCB03023 | | |
| | 48 | | | RCCB03191 | | |
| | 49 | | | RCCB03278 | | |
| | 50 | | | RCCB03452 | | |
| | 51 | | | RCCB03596 | | |
| | 52 | | | RCCB03762 | | |
| | 53 | | | RCCB03972 | | |
| | 54 | | | RCCB04165 | | |
| | 55 | | | RCCB04383 | | |
| | 56 | | | RCCB04571 | | |
| | 57 | | | RCCB04585 | | |
| | 58 | | | RCCB05780 | | |
| | 59 | | | RCCB05975 | | |
| | 60 | | | RCCB06304 | | |
| | 61 | | | RCCB06305 | | |
| Electron transfer | 62 | Pyridine nucleotide-disulphide oxidoreductases | | RCCB00442 | | NADH dehydrogenase, not part of an operon |

TABLE 3-continued

Clostridium carboxidivorans genes used in metabolic engineering.

| Pathway | Gene ID | Gene Name | EC Number | ORF ID | Copy ID | Description |
|---|---|---|---|---|---|---|
| | 63 | | | RCCB01674 | | NADH dehydrogenase, not part of an operon |
| | 64 | | | RCCB03510 | | next to cooF and cooS, probably important for reduced pyridine cofactor generation |
| | 65 | | | RCCB00586 | | NADH dehydrogenase, not part of an operon |
| | 66 | | | RCCB04795 | | NADH: ferredoxin oxidoreductase, not part of an operon |
| | 67 | Membrane-associated electron transfer FeS protein, cooF | | RCCB03509 | cooF | Between gene number 2 and gene number 64 |

Genes that code for enzymes in the electron transfer pathway include carbon monoxide dehydrogenase, Enzyme Commission number (EC 1.2.2.4). Five separate open reading frame (ORF) sequences were identified in *C. ragsdalei* and *C. ljungdahlii*, and six were identified in the *C. carboxidivorans* genome for the carbon monoxide dehydrogenase enzyme.

Figure 3:
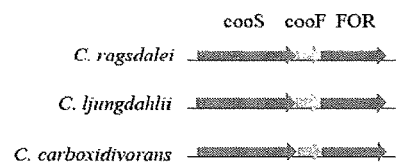
FIG. 3 is a diagram illustrating a genetic map containing the location of one of the carbon monoxide dehydrogenase (CODH) operons which includes cooS, cooF and a ferredoxin oxidoreductase (FOR), in accordance with the invention.
Figure 8:
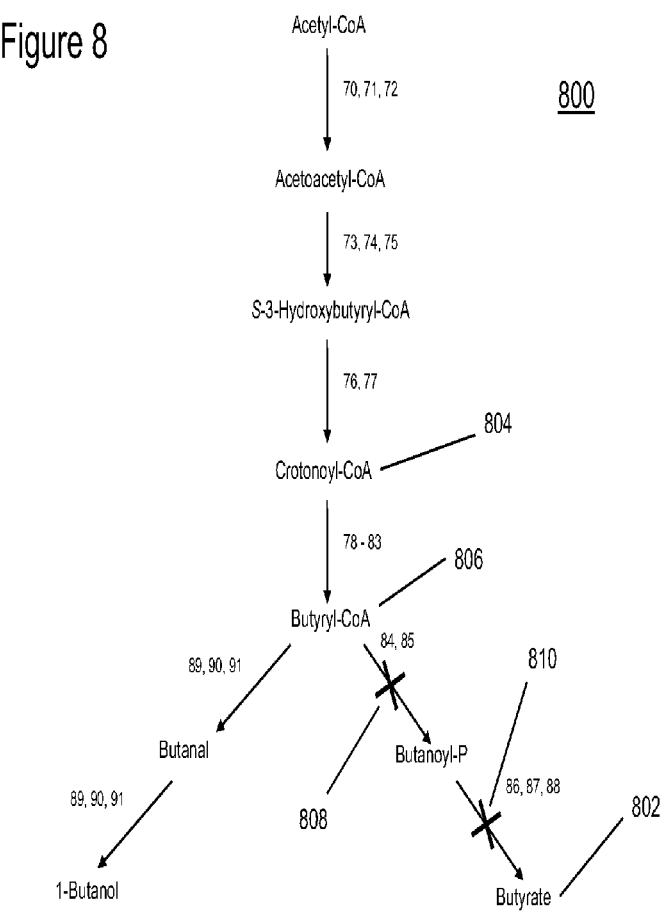
FIG. 8 is a diagram of the butanol and butyrate biosynthesis pathway in *C. carboxidivorans* and the corresponding genes catalyzing the conversion of acetyl-CoA to butanol and butyrate showing a strategy for increasing butanol production, in accordance with the invention.

FIG. 3 is a diagram of carbon-monoxide dehydrogenase operon 300. The gene order within operon 300 is highly conserved in all three species of acetogenic Clostridia, and comprises the genes coding for the carbon monoxide dehydrogenase (cooS) (Gene ID 4, Tables 1, 2, and 3), followed by the membrane-associated electron transfer FeS protein (cooF) (Gene ID 55, Table 1; Gene ID 51, Table 2; Gene ID 67, Table 3), in turn, followed by ferredoxin oxidoreductase (FOR).

A comparison was conducted of the genetic sequence found in the operon of FIG. 3 across the three species of acetogenic Clostridia. The cooS gene had 98% identity between *C. ragsdalei* and *C. ljungdahlii*, 84% identity between *C. carboxydivorans* and *C. ragsdahlii*, and 85% identity between *C. carboxydivorans* and *C. ljungdahlii*. The cooF gene had 98% identity between *C. ragsdalei* and *C. ljungdahlii*, 80% identity between *C. carboxydivorans* and *C. ragsdalei*, and 81% identity between *C. carboxydivorans* and *C. ljungdahlii*. The FOR gene had 97% identity between *C. ragsdalei* and *C. ljungdahlii*, 77% identity between *C. carboxydivorans* and *C. ragsdalei*, and 77% identity between *C. carboxydivorans* and *C. ljungdahlii*.

Six hydrogenase (EC 1.12.7.2) ORF sequences were identified in the genome of each of the acetogenic *Clostridium* species.

Twelve ferredoxin biosynthesis genes (Gene ID 40-51) were identified in the *C. ragsdalei* genome. Eleven ferredoxin biosynthesis genes (Gene ID 37-47, Table 2) were found in *C. ljungdahlii*, and twenty-six (Gene ID 36-61, Table 3) were found in *C. carboxidivorans*.

Three genes coding for ferredoxin oxidoreductase enzymes were found in the *C. ragsdalei* genome that contain both a ferredoxin and nicotinamide cofactor binding domain. The ORF Sequence ID numbers (Table 1) for these genes are: RCCCO2615; RCCCO2028; and RCCCO3071. The key gene for metabolic engineering, RCCCO2028, is part of the cooS/cooF operon, also shown in FIG. 3. Similarly, three genes coding for ferredoxin oxidoreductase (FOR) enzymes were found in the *C. ljungdahlii* genome. Each of these genes code for both the ferredoxin and cofactor binding domains. The ORF Sequence ID numbers for these genes are: RCCD00185; RCCD01847; and RCCD00433 (Table 2). The key gene RCCD01847, is part of the cooF/cooS operon shown in FIG. 3.

Five genes were found in the *C. carboxidivorans* genome that contain both the ferredoxin and cofactor binding domains. The ORF Sequence ID numbers (Table 3) for these genes are: RCCB00442; RCCB01674; RCCB03510; RCCB00586; and RCCB 04795. The potentially key gene for modulating electron flow is RCCB03510, which is part of the cooF/cooS operon (FIG. 3).

The genes encoding AR (Gene ID 21, Table 1; Gene ID 19, Table 2) were sequenced in *C. ragsdalei* and *C. ljungdahlii*. A high degree of gene conservation is observed for the acetyl CoA reductase gene in *C. ragsdalei* and *C. ljungdahlii*. Furthermore, in both micro-organisms, the enzyme exhibits a high degree of homology. The sequence of the acetyl CoA gene in *C. ragsdalei* and *C. ljungdahlii* was compared and found to have a 97.82% identity.

Further, the functionality of the gene (including the promoter) encoding for acetyl CoA reductase was tested. The gene was amplified by PCR, transferred into shuttle vector pCOS52 and ligated into the EcoRI site to form pCOS54. The vector contained the entire acetyl-CoA reductase gene and its promoter on a high-copy plasmid. pCOS52 contained the same backbone vector as pCOS54 but lacked the AR gene. pCOS52 was used as the control plasmid in functional assays to determine expression of the AR gene in *E. coli* to confirm the Clostridial gene function. The results confirmed the function of the acetyl CoA reductase gene.

The functional assay consisted of adding cells harvested at the given time points to a reaction buffer containing NADPH and acetone as the substrate. Spectrophotometric activity (conversion of NADPH to NADP+) was measured at 378 nm and compared to a standard curve to determine total activity level. Specific activity was determined using 317 mg/gram of dry cell weight at an OD measurement of 1.

The genes encoding the PTA-ACK operon (Gene IDs 16-17, Tables 1 and 3; Gene IDs 15-16, Table 2) and its promoter were sequenced in C. ragsdalei, C. ljungdahlii, and C. carboxydivorans. The functionality of the operon was confirmed, and it was demonstrated that downregulation of the operon increases the ethanol to acetate production ratio. Downregulation involves decreasing the expression of the transcription of the 2-gene operon via promoter modification through site-directed mutagenesis. Such downregulation leads to a decrease in mRNA, leading to a decrease in protein production and a corresponding decrease in the ability of the strain to produce acetate. Such downregulation can be achieved via the method described in Example 2.

Additionally, a comparison was conducted of the genetic sequence found in the PTA-ACK operon across three species of acetogenic Clostridia. The PTA gene had 97% identity between C. ragsdalei and C. ljungdahlii, 78% identity between C. carboxydivorans and C. ragsdalei, and 79% identity between C. ljungdahlii and C. carboxydivorans. The ACK gene had 96% identity between C. ragsdalei and C. ljungdahlii, 78% between C. carboxydivorans and C. ragsdalei, and 77% between C. carboxydivorans and C. ljungdahlii.

Key genes to promote production of ethanol in C. ragsdalei include: SEQ ID NO 1 (Gene ID Nos. 4, 55, 53, Table 1) the gene sequence, including the experimentally determined promoter region, for carbon monoxide dehydrogenase, cooS, electron transfer protein cooF, and the NADH dependent ferredoxin oxidoreductase (FOR);
SEQ ID NO 2 (Gene ID Nos. 17, 16, Table 1), the gene sequence, including the experimentally determined promoter region, for ACK and PTA;
SEQ ID NO 3 (Gene ID No. 6, Table 1), the gene sequence, including the experimentally determined promoter region, for the acetyl CoA reductase;

```
Sequence Listing
C. ragsdalei gene sequences (Table 1)
>SEQ ID NO. 1: (cooS, cooF, NADH: Ferredoxin
Oxidoreductase operon (includes STOP),
Gene ID Nos. 4, 55, 53)
TATTATATCAATATAGAATAATTTTCAATCAAATAAGAATTATTTTATA

TTTTATATTGACAAGGAAACCGAAAAGGTTTATATTATTGTTATTGGAT

AACAATTATTTTTTAGTTAGTTGTACTTGTAAATAAATAGTATTAATTA

ATACTATTAAACTATTACAGTTTTTGATTCTTAGTATAAGTATTCTTAG

TATCTTTAGCACTTAGAATACGTTATCCTTTAGGAGAATAATCCTAATC

AGTAATTTTAATAATTTAATAGTATACTTAAATAGTATAGTTTGGAGGT

TTTATTATGTCAAATAACAAAATTTGTAAGTCAGCAGATAAGGTACTTG

AAAAGTTTATAGGTTCTCTAGATGGTGTAGAAACTTCTCATCATAGGGT

AGAAAGCCAAAGTGTTAAATGTGGTTTTGGTCAGCTAGGAGTCTGCTGT

AGACTCTGTGCAAACGGTCCCTGCAGAATAACACCTAAAGCTCCAAGAG

GAGTATGTGGTGCTAGTGCTGATACCATGGTTGCAAGAAACTTTCTTAG

AGCTGTAGCTGCCGGCAGTGGATGTTATATCCATATAGTCGAAAATACA

GCTAGAAACGTAAAATCAGTAGGTGAAACCGGCGGAGAGATAAAAGGAA

TGAATGCTCTCAACACCCTAGCAGAAAAACTTGGTATAACAGAATCTGA

CCCACATAAAAAGCTGTACTAGTAGCTGTGCCGTATTAAAGGACTTAT

ACAAACCAAAATTCGAAAAAATGGAAGTTATAAATAAATTAGCTTATGC

ACCTAGACTAGAAAATTGGAACAAATTAAATATAATGCCTGGCGGTGCA

AAATCAGAAGTTTTTGATGGTGTAGTAAAAACTTCTACAAATCTAAACA

GCGACCCTGTAGATATGCTTCTAAATTGTTTAAAACTTGGAATATCCAC

TGGGATTTACGGACTTACCCTTACAAATTTATTAAATGACATAATTTTA

GGTGAACCTGCTATAAGACCTGCAAAAGTTGGTTTTAAAGTTGTAGATA

CGGATTATATAAATTTGATGATAACAGGCCACCAGCACTCCATGATTGC

CCACCTTCAAGAAGAACTTGTAAAACCTGAAGCTGTAAAAAAAGCCCAA

GCAGTTGGTGCTAAAGGATTCAAACTAGTTGGATGTACCTGTGTCGGAC

AGGATTTACAGTTAAGAGGTAAATACTATACTGATGTTTTCTCCGGTCA

TGCAGGAAATAACTTTACAAGTGAAGCCTTAATAGCAACTGGAGGTATA

GATGCAATAGTATCTGAATTTAACTGTACTCTTCCTGGCATCGAGCCAA

TAGCTGATAAGTTCATGGTTAAAATGATATGCCTAGATGACGTTTCTAA

AAAATCAAATGCAGAATATGTAGAATACTCTTTTAAAGATAGAGAAAAA

ATAAGCAACCATGTTATAGATACGGCTATTGAAAGTTATAAGGAAAGAA

GATCTAAAGTTACAATGAATATTCCTAAAAACCATGGCTTTGATGACGT

CATAACAGGTGTAAGTGAAGGTTCCTTAAAATCCTTCTTAGGCGGAAGT

TGGAAACCTCTTGTAGACTTAATTGCTGCTGGAAAAATTAAAGGTGTTG

CTGGAATAGTAGGTTGTTCAAACTTAACTGCCAAAGGTCACGATGTATT

TACAGTAGAACTTACAAAAGAACTCATAAAGAGAAATATAATTGTACTT

TCTGCAGGTTGTTCAAGTGGTGGACTTGAAAATGTAGGACTTATGTCTC

CAGGAGCTGCTGAACTTGCAGGAGATAGCTTAAAAGAAGTATGTAAGAG

CCTAGGTATACCACCTGTACTAAATTTTGGTCCATGTCTTGCTATTGGA

AGATTGGAAATTGTAGCAAAAGAACTAGCAGAATACCTAAAAATAGATA

TTCCACAGCTTCCACTTGTGCTTTCTGCACCTCAATGGCTTGAAGAACA

AGCATTGGCAGATGGAAGTTTTGGTCTTGCCCTTGGATTACCACTTCAC

CTTGCTATATCTCCTTTCATTGGTGGAAGCAAAGTGGTAACAAAAGTTT

TATGTGAAGATATGGAAAATCTAACAGGCGGCAAGCTTATAATAGAAGA

CGATGTAATAAAAGCTGCAGATAAATTAGAAGAAACCATACTTGCAAGA

AGGAAAAGCTTAGGTCTTAATTAAATGAAAAGAATAATGATAAATAAGG

ATTTATGTACCGGATGCTTAAATTGTACTTTAGCTTGTATGGCAGAACA

CAATGAAAATGGGAAATCTTTTTATGATCTGGATCTCAGCAATAAATTT

CTTGAAAGTAGAAATCATATATCTAAAGATGATAATGGAAACAAGCTTC

CTATATTTTGCCGTCACTGTGACGAACCTGAGTGCGTAATGACATGTAT

GAGCGGTGCCATGACTAAAGATCCTGAAACTGGTATAGTATCCTATGAT

GAGCATAAATGTGCCAGCTGCTTTATGTGCGTCATGTCCTGTCCTTATG
```

-continued

GAGTATTGAAACCAGATACTCAGACCAAAAGTAAAGTAGTTAAATGTGA

CCTGTGTGGTGACAGAGATACACCTAGATGCGTTGAAAATTGTCCAACA

GAAGCAATTTATATTGAAAAGGAGGCAGATCTCCTATGAATGAGTGGTT

TAACAATAAAAATATTTTTTCACACAAAATATGTAATAATAGGAGCCAG

TGCTGCTGGAATAAATGCTGCTAAAACTTTAAGAAAGTTAGATAAATCC

TCCAAAATAACTATTATTTCAAAGGATGATGCAGTTTATTCAAGATGTA

TACTCCACAAAGTACTTGAGGGAAGTAGAAATTTAGATACCATAAATTT

TGTAGATTCTGATTTCTTTGAAAAAAATAATATAGAATGGATAAAAGAT

GCAGATGTAAGCAATATTGATATTGACAAGAAAAAAGTCTTACTTCAAG

ACAACAGCAGCTTCAAATTTGACAAGCTCCTTATAGCTTCTGGTGCTTC

CTCCTTTATTCCCCCAGTTAAAAAATTAAGAGAAGCTAAAGGAGTGTAC

TCCCTTAGAAATTTTGAAGATGTAACTGCTATACAAGACAAACTTAAAA

ACGCAAAACAAGTGGTAATACTTGGTGCAGGTCTTGTAGGAATTGATGC

ACTTTTAGGTCTTATGGTGAAAAATATAAAGATTTCAGTTGTAGAAATG

GGAGATAGGATTCTCCCCCTTCAACTGGACAAAACTGCATCCACTATAT

ATGAAAAGTTGTTAAAAGAAAAAGGTATAGATGTCTTTACTTCAGTTAA

ATTGGAAGAGGTAGTTTTAAATAAAGACGGAACTGTAAGTAAAGCAGTA

CTATCAAATTCAACTTCTATAGATTGCGATATGATAATAGTTGCTGCTG

GTGTTAGACCAAATGTAAGCTTTATAAAAGACAGCAGGATAAAAGTTGA

AAAAGGCATTGTCATAGACAAACATTGTAAAACCACTGTAGATAATATA

TATGCTGCAGGAGATGTTACTTTTACTGCTCCATATGGCCTATAGCTGT

AAAGCAGGGAATAACTGCTGCTTACAACATGGTAGGTATAAATAGAGAA

TTACATGACACTTTTGGCATGAAGAACTCAATGAATTTATTTAACCTTC

CATGCGTATCCCTTGGTAATGTAAATATAGCAGATGAAAGTTATGCTGT

TGATACATTAGAAGGAGATGGAGTTTATCAAAAAATAGTTCACAAAGAT

GGAGTAATCTACGGTGCACTTCTAGTTGGAGATATATCTTACTGCGGCG

TACTAGGATATCTCATAAAAAATAAAGTAAATATAAGCAATATCCATAA

AAATATTTTTGACATAGATTATTCTGATTTTTACAATGTTGAAGAAGAT

GGACAATATAGTTATCAATTGAGGTAA

SEQ ID NO. 2: (PTA-ACK operon (includes STOP), Gene ID Nos. 17, 16)
GCATACTGATTGATTATTTATTTGAAAATGCCTAAGTAAAATATATACA

TATTATAACAATAAAATAAGTATTAGTGTAGGATTTTTAAATAGAGTAT

CTATTTTCAGATTAAATTTTTACTTATTTGATTTACATTGTATAATATT

GAGTAAAGTATTGACTAGTAAAATTTTGTGATACTTTAATCTGTGAAAT

TTCTTAGCAAAAGTTATATTTTTGAATAATTTTTATTGAAAAATACAAC

TAAAAAGGATTATAGTATAAGTGTGTGTAATTTTGTGTTAAATTTAAAG

GGAGGAAATAAACATGAAATTGATGGAAAAAATTTGGAATAAGGCAAAG

GAAGACAAAAAAAGATTGTCTTAGCTGAAGGAGAAGAAGAAAGAACTC

TTCAAGCTTGTGAAAAAATAATTAAAGAAGGTATTGCAAATTTAATCCT

TGTAGGGAATGAAAAGGTAATAGAGGAGAAGGCATCAAAATTAGGCGTA

AGTTTAAATGGAGCAGAAATAGTAGATCCAGAAACCTCGGATAAACTAA

AAAAATATGCAGATGCTTTTTATGAATTGAGAAAGAAGAAGGGAATAAC

ACCAGAAAAAGCGGATAAAATAGTAAGAGATCCAATATATTTTGCTACG

ATGATGGTTAAGCTTGGAGATGCAGATGGATTGGTTTCAGGTGCAGTGC

ATACTACAGGTGATCTTTTGAGACCAGGACTTCAAATAGTAAAGACAGC

TCCAGGTACATCAGTAGTTTCCAGCACATTTATAATGGAAGTACCAAAT

TGTGAATATGGTGACAATGGTGTACTTCTATTTGCTGATTGTGCTGTAA

ATCCATGCCCAGATAGTGATCAATTGGCTTCAATTGCAATAAGTACAGC

AGAAACTGCAAAGAACTTATGTGGAATGGATCCAAAAGTAGCAATGCTT

TCATTTCTACTAAGGGAAGTGCAAAACACGAATTAGTAGATAAAGTTA

GAAATGCTGTAGAAATTGCCAAAAAAGCTAAACCAGATTTAAGTTTGGA

CGGAGAATTACAATTAGATGCCTCTATCGTAGAAAAGGTTGCAAGTTTA

AAGGCTCCTGAAAGTGAAGTAGCAGGAAAAGCAAATGTACTTGTATTTC

CAGATCTCCAAGCAGGAAATATAGGTTATAAACTTGTTCAAAGATTTGC

AAAAGCTGATGCTATAGGACCTGTATGCCAGGGATTTGCAAAACCTATA

AATGATTTGTCAAGAGGATGTAACTCCGATGATATAGTAAATGTAGTAG

CTGTAACAGCAGTTCAGGCACAAGCTCAAAAGTAAATGAAAATATTAGT

AGTAAACTGTGGAAGTTCATCTTTAAAATATCAACTTATTGATATGAAA

GATGAAAGCGTTGTGGCAAAAGGACTTGTAGAAAGAATAGGAGCAGAAG

GTTCAGTTTTAACACATAAAGTTAACGGAGAAAAGTTTGTTACAGAGCA

GCCAATGGAAGATCATAAAGTTGCTATACAATTAGTATTAAATGCTCTT

GTAGATAAAAAACATGGTGTAATAAAAGATATGTCAGAAATATCTGCTG

TAGGGCATAGAGTTTTGCATGGTGGAAAAAAATATGCGGCATCCATTCT

TATTGATGACAATGTAATGAAAGCAATAGAAGAATGTATTCCATTAGGA

CCATTACATAATCCAGCTAATATAATGGGAATAGATGCTTGTAAAAAAC

TAATGCCAAATACTCCAATGGTAGCAGTATTTGATACAGCATTTCATCA

GACAATGCCAGATTATGCTTATACTTATGCAATACCTTATGATATATCT

GAAAAGTATGATATCAGAAAATATGGTTTTCATGGAACTTCTCATAGAT

TCGTTTCAATTGAAGCAGCCAAGTTGTTAAAGAAAGATCCAAAAGATCT

TAAGCTAATAACTTGTCATTTAGGAAATGGAGCTAGTATATGTGCAGTA

AACCAGGGAAAAGCAGTAGATACAACTATGGGACTTACTCCCCTTGCAG

GACTTGTAATGGGAACTAGATGTGGTGATATAGATCCAGCTATAATACC

ATTTGTAATGAAAAGAACAGGTATGTCTGTAGATGAAATGGATACTTTA

ATGAACAAAAGTCAGGAATACTTGGAGTATCAGGAGTAAGCAGCGATT

TTAGAGATGTAGAAGAAGCTGCAAATTCAGGAAATGATAGAGCAAAACT

TGCATTAAATATGTATTATCACAAGTTAAATCTTTCATAGGAGCTTAT

GTTGCAGTTTTAAATGGAGCAGATGCTATAATATTTACAGCAGGACTTG

GAGAAAATTCAGCTACTAGCAGATCTGCTATATGTAAGGGATTAAGCTA

TTTTGGAATTAAAATAGATGAAGAAAAGAATAAGAAAAGGGGAGAAGCA

CTAGAAATAAGCACACCTGATTCAAAGATAAAAGTATTAGTAATTCCTA

-continued

CAAATGAAGAACTTATGATAGCTAGGGATACAAAAGAAATAGTTGAAAA

TAAATAA

SEQ ID NO. 3: (ORF RCCCO2715, P11, NADPH-SADH
(includes STOP), Gene ID No. 6)
ATGAAAGGTTTTGCAATGTTAGGTATTAACAAGTTAGGATGGATTGAAA

AGAAAAACCCAGTACCAGGTCCTTATGATGCGATTGTACATCCTCTAGC

TGTATCCCCATGTACATCAGATATACATACGGTTTTTGAAGGAGCACTT

GGTAATAGGGAAAATATGATTTTAGGTCACGAAGCTGTAGGTGAAATAG

CTGAAGTTGGCAGTGAAGTTAAAGATTTTAAAGTTGGCGATAGAGTTAT

CGTACCATGCACAACACCTGACTGGAGATCCTTAGAAGTCCAAGCTGGT

TTTCAACAGCATTCAAACGGTATGCTTGCAGGATGGAAGTTTTCCAATT

TTAAAGACGGTGTATTTGCAGATTACTTTCATGTAAACGATGCAGATAT

GAATCTTGCAATACTTCCAGATGAAATACCTTTAGAAAGTGCAGTTATG

ATGACAGACATGATGACTACTGGTTTTCATGGGGCAGAACTTGCTGACA

TAAAAATGGGTTCCAGTGTTGTCGTAATTGGTATAGGAGCTGTTGGATT

AATGGGAATAGCCGGTTCCAAACTTCGAGGAGCAGGTAGAATTATCGGT

GTTGGAAGCAGACCCGTTTGTGTTGAAACAGCTAAATTTTATGGAGCAA

CTGATATTGTAAATTATAAAAATGGTGATATAGTTGAACAAATAATGGA

CTTAACTCATGGTAAAGGTGTAGACCGTGTAATCATGGCAGGCGGTGGT

GCTGAAACACTAGCACAAGCAGTAACTATGGTTAAACCTGGCGGCGTAA

TTTCTAACATCAACTACCATGGAAGCGGTGATACTTTGCCAATACCTCG

TGTTCAATGGGCTGCGGCATGGCTCACAAAACTATAAGAGGAGGGTTA

TGTCCCGGCGGACGTCTTAGAATGGAAATGCTAAGAGACCTTGTTCTAT

ATAAACGTGTTGATTTGAGCAAACTTGTTACTCATGTATTTGATGGTGC

AGAAAATATTGAAAAGGCCCTTTTGCTTATGAAAAATAAGCCAAAAGAT

TTAATTAAATCAGTAGTTACATTCTAA

Using detailed genomic information, the acetogenic Clostridia micro-organisms have been metabolically engineered to increase the carbon and electron flux through the biosynthetic pathways for ethanol and butanol, while simultaneously reducing or eliminating carbon and electron flux through the corresponding acetate and butyrate formation pathways, in accordance with the present invention. For this purpose, the activities of key genes encoding for enzymes in the pathway have been modulated. In one embodiment, gene expression of key alcohol producing enzymes is increased by increasing the copy number of the gene. For example, a key carbon monoxide dehydrogenase operon (FIG. 3) and the associated electron transfer proteins, including acetyl CoA reductase and aldehyde ferredoxin oxidoreductase are duplicated within the genome of the modified organism. In one embodiment, these duplications are introduced into strains having knocked out or attenuated acetate production to further channel electrons into the ethanol or butanol production pathway. In another embodiment a knockout strategy is applied to strains of acetogenic Clostridia that, when grown on syngas, produce more complex mixtures of alcohols and acids, such as ethanol, butanol and hexanol and their corresponding carboxylic acids.

In one embodiment, vectors to be used for the transfer of acetogenic Clostridia cloned genes from cloning vehicles to parent acetogenic Clostridia strains are constructed using standard methods (Sambrook et al., 1989). All gene targets used in molecular genetics experiments are amplified using high-fidelity polymerase chain reaction (PCR) techniques using sequence-specific primers. The amplified genes are next subcloned into intermediate cloning vehicles, and later recombined in multi-component ligation reactions to yield the desired recombinant vector to be used in the gene transfer experiments. The vectors contain the appropriate functional features required to carry out the gene transfer experiments successfully and vary depending on the method used.

To transfer the recombinant vectors into recipient acetogenic Clostridia, a variety of methods are used. These include electroporation, bi-parental or tri-parental conjugation, liposome-mediated transformation and polyethylene glycol-mediated transformation. Recombinant acetogenic Clostridia are isolated and confirmed through molecular biology techniques based on the acquisition of specific traits gained upon DNA integration.

Example 1

Acetogenic Clostridia contain operon 300, shown in FIG. 3, that consists of carbon monoxide dehydrogenase 104 (cooS, Gene ID 4, Table 1, Table 2, Table 3), a membrane-associated electron transfer protein (cooF), and a ferredoxin oxidoreductase (FOR). Overexpression of carbon monoxide dehydrogenase 104 within the acetogenic Clostridia is known to increase electron flow from syngas components to the oxidized nucleotide cofactors $NAD^+$ and $NADP^+$ The increased levels of reduced nucleotide cofactors then stimulate generation of intermediate compounds in Wood-Ljungdahl pathway 100.

In one embodiment, operon 300 is amplified using long-PCR techniques with primers that are designed to anneal to a region 200 nucleotides (nt) upstream of the carbon monoxide dehydrogenase gene and 200 nt downstream of the ferredoxin oxidoreductase gene. The total region is about 3.8 kilobase pairs. The amplified DNA is cloned directly into suitable plasmid vectors specifically designed to ligate PCR products such as pGEM T easy (Promega, Madison, Wis.) or pTOPO (Invitrogen, Carlsbad, Calif.). The ends of the PCR product contain engineered restriction sites to facilitate later cloning steps. The operon 300 is subcloned into a vector that already contains cloned chromosomal C. ragsdalei or other acetogenic Clostridial DNA to allow chromosomal integration at a neutral site.

Example 2

Because carboxylic acids compete with alcohols for electrons, decreasing acid production allows more electrons to flow down the alcohol-production pathway from the CoA intermediate directly to the alcohol. Acetogenic Clostridia contain genes for phospho-transacetylase enzyme (Gene ID 17, Tables 1 and 3; Gene ID 16, Table 2) that converts acetyl-CoA to acetyl-phosphate and acetate kinase (Gene ID 16, Table 1) that converts acetyl-phosphate 218 to acetate 214. In one embodiment, genetic modifications to delete all or part of the genes for both enzymes and knock out or attenuate production of acetate are made as shown in FIG. 5.

Using PCR and other standard methods, a recombinant vector containing two large non-contiguous segments of DNA is generated. Upon replacement of the native gene by the recombinant vector gene, the Clostridial strain contains no phosphotransacetylase or acetate kinase activities as shown in FIG. 5 by X 504 and X 502, respectively.

Modulation of the common promoter region, P* 506 to attenuate gene expression of phosphotransacetylase 508 and acetate kinase 510 and subsequent acetate production are carried out by generating a series of recombinant vectors with altered promoter regions. The vector series is constructed by site-directed mutagenesis.

Additionally, down-regulation of the 2-gene operon containing pta/ack genes is performed by site-directed mutagenesis of the promoter region. A decrease in RNA polymerase binding leads to a decrease in transcriptional activity off of the pta/ack promoter and in turn lead to a decrease in protein activity. The end result is a decrease in acetate production since the intermediates are produced at a lower rate and more carbon from acetyl-CoA goes towards ethanol production. A promoter probe assay using a reporter group that is easily quantitated has been developed to measure relative promoter strength of the pta/ack promoter in vivo. After site-directed mutagenesis is performed, which imparts single and multiple lesions over a 200 base pair region, strains that have decreased promoter activity are isolated such that a series of strains with 90%, 80%, 70%, 60%, 50%, 40%, 30%, 20%, 10% and 0% activity of the native promoter in the assay are isolated and tested in recombinant Clostridia strains.

Example 3

In vivo, the acetyl CoA enzyme designated in 102 and FIG. 5 converts the Coenzyme A (CoA) form of a carbon moiety, such as acetyl-CoA 102 or butyrl-CoA directly to its corresponding alcohol. Thermodynamically, direct conversion from the CoA form to the alcohol requires transfer of four electrons, and is a more efficient way to generate the alcohol, compared to the two-step conversion of the carboxylic acid to the corresponding alcohol. For example, as shown in FIG. 6, the two step conversion requires that acetate 214, first be converted to its aldehyde form (acetaldehyde, 604), and then to the corresponding alcohol, ethanol 216. Thus, increasing AR activity, portrayed by the vertical arrow 602 is desirable for increasing alcohol production, and increasing the selectivity of the process by increasing the ratio of alcohol to acid.

In one embodiment, AR activity in acetogenic Clostridia is increased by amplifying the gene in vitro using high-fidelity PCR and inserting the duplicated copy of the gene into a neutral site in the chromosome using standard molecular genetic techniques. After gene replacement of the vector, the chromosome contains two copies of the AR. Confirmation of gene replacement followed by gene expression studies of the recombinant strain are performed and compared to the parent strain.

In other embodiments a similar strategy is used to increase the enzymatic activity of adhE-type alcohol dehydrogenases, short-chain alcohol-dehydrogenases and primary Fe-containing alcohol dehydrogenases.

Example 4

Under some conditions, Clostridia need to obtain additional energy in the form of adenosine triphosphate production (ATP) causing the cells to temporarily increase the production of acetate 214 from acetyl-CoA 102. The net reaction is 1 ATP from ADP+P, through acetyl-phosphate. Acetate production is advantageous to the syngas fermentation process at low to moderate acetic acid concentrations, because it allows the cells to produce more energy and remain robust. However, too much free acetic acid causes dissipation of the transmembrane ion gradient used as the primary ATP generation source and therefore becomes detrimental to the cells. For industrial production purposes, it is advantageous to convert the acetate to ethanol to increase ethanol production and reduce the probability of accumulating too much free acetic acid.

In one embodiment, ethanol production in the double mutant *C. ragsdalei* strain is increased by between 10 and 40% as a result of the increased aldehyde ferredoxin oxidoreductase and AR activities. In another embodiment, the ratio of ethanol to acetate produced is increased between 5 and 10 fold, but allows sufficient acetate formation to support ATP production needed to meet the energy needs of the microorganism.

While the invention has been described with reference to particular embodiments, it will be understood by one skilled in the art that variations and modifications may be made in form and detail without departing from the spirit and scope of the invention.

What is claimed is:

1. A method of producing ethanol comprising: isolating and purifying anaerobic, ethanologenic microorganisms comprising an isolated polynucleotide comprising a nucleotide sequence encoding an operon that codes for acetate kinase, phosphotransacetylase, and a promoter, said sequence at least 97% identical to SEQ ID NO 2; and fermenting syngas with said microorganisms in a fermentation bioreactor.

2. A method of increasing ethanologenesis in a microorganism comprising an isolated polynucleotide comprising a nucleotide sequence encoding an operon that codes for acetate kinase, phosphotransacetylase, and a promoter, said sequence at least 97% identical to SEQ ID NO 2, said method comprising: modifying or downregulating a promoter region of said nucleotide sequence to decrease the activity of the operon or to cause underexpression of the operon.

* * * * *